(12) United States Patent
Limbach et al.

(10) Patent No.: US 8,263,813 B2
(45) Date of Patent: Sep. 11, 2012

(54) METHOD FOR ISOMERIZING OLEFINICALLY UNSATURATED ALCOHOLS

(75) Inventors: Michael Limbach, Worms (DE); Joaquim Henrique Teles, Otterstadt (DE); Radwan Abdallah, Ludwigshafen (DE); Torsten Mäurer, Lambsheim (DE); Thorsten Johann, Limburgerhof (DE); Manuel Danz, Eppelheim (DE)

(73) Assignee: BASF SE (DE)

( * ) Notice: Subject to any disclaimer, the term of this patent is extended or adjusted under 35 U.S.C. 154(b) by 200 days.

(21) Appl. No.: 12/920,150

(22) PCT Filed: Feb. 27, 2009

(86) PCT No.: PCT/EP2009/052384
§ 371 (c)(1),
(2), (4) Date: Aug. 30, 2010

(87) PCT Pub. No.: WO2009/106622
PCT Pub. Date: Sep. 3, 2009

(65) Prior Publication Data
US 2011/0004032 A1    Jan. 6, 2011

(30) Foreign Application Priority Data
Feb. 28, 2008  (DE) .................. 10 2008 011 767

(51) Int. Cl.
C07C 29/56     (2006.01)
C07C 33/02     (2006.01)
(52) U.S. Cl. ..................... 568/875; 568/906
(58) Field of Classification Search ............. 568/875, 568/906
See application file for complete search history.

(56) References Cited

U.S. PATENT DOCUMENTS

| | | | |
|---|---|---|---|
| 3,697,580 A | 10/1972 | Overwien et al. | |
| 3,915,921 A | 10/1975 | Schlatzer, Jr. | |
| 3,966,687 A | 6/1976 | Ribba et al. | |
| 4,007,135 A | 2/1977 | Hayden et al. | |
| 4,110,403 A | 8/1978 | Ichikawa et al. | |
| 4,117,016 A | 9/1978 | Hughes | |
| 4,154,762 A | 5/1979 | Huang et al. | |
| 4,165,342 A | 8/1979 | Dudeck et al. | |
| 4,310,709 A | 1/1982 | Rebafka | |
| 4,324,699 A | 4/1982 | Mross et al. | |
| 4,395,524 A | 7/1983 | Emmons et al. | |
| 4,432,881 A | 2/1984 | Evani | |
| 4,732,918 A | 3/1988 | Lohmueller et al. | |
| 5,015,708 A | 5/1991 | Shih et al. | |
| 5,149,884 A | 9/1992 | Brenner et al. | |
| 6,013,843 A | 1/2000 | Aquila et al. | |
| 6,015,551 A | 1/2000 | Schade et al. | |
| 6,211,114 B1 | 4/2001 | Brocker et al. | |
| 6,329,483 B1 | 12/2001 | Schade et al. | |
| 6,399,679 B1 | 6/2002 | Meffert et al. | |
| 6,682,725 B1 | 1/2004 | Dieing et al. | |
| 2003/0113285 A1 | 6/2003 | Meffert et al. | |
| 2003/0147929 A1 | 8/2003 | Kim et al. | |
| 2006/0036106 A1 | 2/2006 | Mazanec et al. | |
| 2006/0084586 A1 | 4/2006 | Drzewinski et al. | |
| 2006/0183822 A1 | 8/2006 | Nguyen-Kim et al. | |

FOREIGN PATENT DOCUMENTS

| | | |
|---|---|---|
| DE | 1901709 A1 | 8/1970 |
| DE | 2020865 | 11/1971 |
| DE | 2041976 | 3/1972 |
| DE | 2300512 | 7/1973 |
| DE | 2454972 | 6/1975 |
| DE | 2521906 A1 | 12/1975 |
| DE | 2517859 | 3/1976 |
| DE | 2715209 A1 | 10/1978 |
| DE | 2751766 A1 | 5/1979 |
| DE | 2753359 A1 | 6/1979 |
| DE | 3414717 A1 | 10/1985 |
| DE | 4213971 A1 | 11/1993 |
| EP | 0011356 A1 | 5/1980 |
| EP | 0014457 A2 | 8/1980 |
| EP | 0082609 A1 | 6/1983 |
| EP | 0085237 A1 | 8/1983 |
| EP | 0112261 | 6/1984 |
| EP | 0172565 A2 | 2/1986 |
| EP | 244632 A2 | 11/1987 |
| EP | 0266015 A1 | 5/1988 |
| EP | 0339748 A2 | 11/1989 |
| EP | 357292 A1 | 3/1990 |
| EP | 0357293 A1 | 3/1990 |
| EP | 0415745 A2 | 3/1991 |
| EP | 0 524 557 A | 1/1993 |
| EP | 841090 A2 | 5/1998 |
| EP | 0881206 A1 | 12/1998 |
| EP | 893 117 A2 | 1/1999 |
| EP | 913143 A2 | 5/1999 |
| EP | 0 982 021 A | 3/2000 |
| EP | 1 064 924 A | 1/2001 |

(Continued)

OTHER PUBLICATIONS

Kogan et al. Liquid phase isomerization of isoprenol into prenol in hydrogen environment. Applied Catalysis A: General, vol. 297, 2006, 231-236.*
U.S. Appl. No. 12/297,895, filed Oct. 21, 2008, Maurer et al.
U.S. Appl. No. 12/920,139, filed Aug. 30, 2010, Limbach et al.
U.S. Appl. No. 12/933,441, filed Sep. 20, 2010, Maurer et al.
Abad, A., et al., "Unique gold chemoselectivity for th eaerobic oxidation of allylic alcohols," Chem., Commun. 2006., pp. 3178-3180.
Abad, A., et al., "Catalyst parameters determining activity and selectivity of supported gold nanoparticles for the aerobic oxidation of alcohols: the molecular reaction mechanisn," Chem. Eur. J. 2008, vol. 14, pp. 212-222.

(Continued)

*Primary Examiner* — Sikarl Witherspoon
(74) *Attorney, Agent, or Firm* — Connolly Bove Lodge & Hutz LLP

(57) ABSTRACT

A process for isomerizing olefinically unsaturated alcohols over supported noble metal catalysts with a support based on carbon in an oxygenous atmosphere.

10 Claims, No Drawings

FOREIGN PATENT DOCUMENTS

| | | |
|---|---|---|
| GB | 1338698 | 11/1973 |
| GB | 1413251 | 11/1975 |
| GB | 1512625 | 6/1978 |
| JP | 8268939 A | 10/1996 |
| WO | WO-97/21744 | 6/1997 |
| WO | WO-00/39176 A1 | 7/2000 |
| WO | WO-01/62809 | 8/2001 |
| WO | WO-01/85821 | 11/2001 |
| WO | WO-01/96324 A2 | 12/2001 |
| WO | WO-02/18042 A1 | 3/2002 |
| WO | WO-03/044003 A1 | 5/2003 |
| WO | WO-2004/002971 A1 | 1/2004 |
| WO | WO-2004/030813 A1 | 4/2004 |
| WO | WO-2004/058837 A2 | 7/2004 |
| WO | WO-2008/037693 A1 | 4/2008 |
| WO | WO-2008/098774 A1 | 8/2008 |

OTHER PUBLICATIONS

Kestenbaum, H., "Zur synhese von ethenoxid in einem mikroreaktionssystem," 2004, Dissertationsschrift, Frankfurt, Main, DE.

"Microreactors," Ullmann's Encyclopedia of Industrial Chemistry, Wiley-VCH, Weinheim, DE, 2002, vol. 22, pp. 1-29.

Ullmann's Encyclopedia of Industrial Chemistry (5th Ed.), VCH Verlagsgesellschaft, Weinheim, 1987, vol. A10, pp. 117-135.

* cited by examiner

METHOD FOR ISOMERIZING OLEFINICALLY UNSATURATED ALCOHOLS

CROSS-REFERENCE TO RELATED APPLICATIONS

This application is a national stage application (under 35 U.S.C. §371) of PCT/EP2009/052384, filed Feb. 27, 2009, which claims benefit of German application 10 2008 011 767.6, filed Feb. 28, 2008.

BACKGROUND OF THE INVENTION

The present invention relates to a process for isomerizing olefinically unsaturated alcohols in an oxygenous atmosphere over a supported catalyst. The invention further relates to the use of supported catalysts for isomerizing olefinically unsaturated alcohols.

The isomerization of olefinically unsaturated alcohols, for example of 3-methylbut-3-en-1-ol (isoprenol) to 3-methylbut-2-en-1-ol (prenol), in liquid phase has already been described. In all cases, the conversion is performed under a gentle stream of hydrogen to increase the catalyst lifetime (S. B. Kogan, M. Kalya, N. Froumin, *Appl. Catal. A: General* 2006, 27, 231-236). According to the information in this document, the noble metal catalysts described are deactivated particularly rapidly and is irreversibly in the absence of hydrogen. Even under optimal conditions, according to this document, the conversion achieved with these catalysts is relatively low when high selectivities in the direction of prenol are to be achieved. At low conversions, the unconverted isoprenol has to be removed and reused for economic operation of the process. The use of hydrogen in the isomerization of isoprenol is often disadvantageous, since side reactions such as the hydrogenation of the double bonds to give the saturated system are observed particularly over silica-supported noble metal catalysts. Attempts are made to avoid this by the expensive stabilization of the cationic palladium sites by doping with selenium or cerium.

U.S. Pat. No. 4,117,016 describes, inter alia, the isomerization of unsaturated alcohols in the liquid phase in the presence of catalytic amounts of a homogeneous ruthenium-hydrido complex in the presence of a ligand, and explicitly rules out the presence even of traces of oxygen, in order to ensure catalyst stability. The isomerization of isoprenol to prenol under nitrogen under the conditions specified in this document proceeds only in low yields which are not of economic interest.

WO2008037693 A1 describes, inter alia, the isomerization of 3-methyl-3-buten-1-ol (isoprenol) over a heterogeneous noble metal catalyst to give 3-methyl-2-buten-1-ol (prenol) in the presence of hydrogen. The trimetallic catalyst consists of Pd, Se and Te immobilized on silica. Here, overhydrogenation in the hydrogen atmosphere results in the formation of up to 2.5% isoamyl alcohol. The removal thereof is costly.

DE-A-1901709 describes a process for preparing buten-2-ols from buten-1-ols. The catalysts used are elemental Pd or Pd compounds in a hydrogen atmosphere. In the case of use of pure Pd in the presence of hydrogen, however, the majority of the double bonds of the starting materials are hydrogenated to form the corresponding saturated compound.

The hydrogenation of the double bond is undesired since there are only small boiling point differences between unconverted starting material and hydrogenation product for some butenols. For instance, the boiling point of 3-methylbut-3-en-1-ol is 131.5° C. (101 325 Pa or 1020 mbar), and that of the corresponding hydrogenation product is 130.9° C. (101 325 Pa or 1020 mbar).

DE-A 2751766 and the parallel U.S. Pat. No. 4,310,709 disclose that, in the case of isomerization of 3-buten-2-ols to the corresponding 2-buten-1-ols in the presence of a heterogeneous catalyst based on Pd and Se on carbon in the presence of hydrogen, high proportions of low boilers such as isoprene and butenes are formed in the manner of a retro-Prins reaction.

EP-A 841090 discloses that the isomerization of 3-buten-1-ols to 2-buten-1-ols in the presence of hydrogen succeeds only with low formation of low boilers or hydrogenation products when the heterogeneous Pd catalyst has been doped with 0.001-0.2% by weight of Se, Te or with a mixture of both metals. Thus, selectivities of up to 94% can be achieved at a conversion of 55%.

*Can. J. Chem.* 1968, 46, 2225-2232 discloses the thermal isomerization of unsaturated alcohols without catalyst. At the high temperatures required, partial resinification of the starting compounds is observed.

According to the teaching of JP-A-8268939, prenol is isomerized to isoprenol in the gas phase in the presence of catalytic amounts of MgO. The temperatures are very high at 150-300° C. and lead to the decomposition of the labile reactants and products. For safety reasons, the reaction is explicitly performed under protective gas (nitrogen). It is possible to achieve selectivities of up to 98% at conversions of 64%.

In spite of several known processes for isomerizing unsaturated alcohols, more particularly including isoprenol to prenol, there was therefore a need to provide a corresponding process which is firstly performable in a simple manner in terms of process technology and secondly delivers good conversions and selectivities in the direction of the desired products.

BRIEF SUMMARY OF THE INVENTION

This object is achieved by the process according to the invention as per claim 1. Preferred embodiments are evident from the dependent claims and the description which follows and the examples.

In the process according to the invention, olefinically unsaturated alcohols are isomerized, the isomerization being performed over a supported noble metal catalyst in an oxygenous atmosphere.

DETAILED DESCRIPTION OF THE INVENTION

The noble metals used are preferably Au, Cu, Ag, Pd, Pt, Rh, Ru, W or Os, particular preference being given to palladium (Pd) or gold (Au) or mixtures of Au or Pd and the other noble metals mentioned.

In the isomerization of isoprenol to prenol, particularly advantageous noble metals have been found to be Pd or Au, or mixtures of Pd and Au.

The support material of the catalyst used in the process according to the invention is preferably a material based on carbon. Merely by way of example for such materials, various types of carbon or various types of graphite are mentioned, as known to those skilled in the art and described in the literature.

In principle, suitable preferred support materials based on carbon are all carbon materials known to those skilled in the art for such uses. The support materials can preferably be used in the form of moldings, granules, extrudates, pellets, spall, tablets or prills. The BET surface area of the support materials (25° C.) is typically in the range from 1 to 10 000 and preferably from 10 to 5000 m²/g, but is not critical in most cases for the process according to the invention.

In the recent past, carbon nanofibers have also been found to be advantageous as catalyst supports for some reactions, as known to those skilled in the art and described in the literature.

In the process according to the invention, it is possible to isomerize especially beta, gamma (β,γ)-unsaturated alcohols to α,β-unsaturated alcohols. In this case, the reaction can be shown schematically as follows:

By way of example, suitable β,γ-unsaturated alcohols here include those of the general formula I

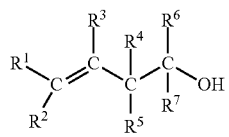

where the substituents $R^1$ to $R^7$ may each independently be hydrogen, a $C_1$-$C_{18}$-alkyl group, an optionally substituted $C_3$-$C_8$-cycloalkyl group or an optionally substituted $C_6$-$C_{18}$-aryl group.

Useful substituents on the cycloalkyl or aryl groups preferably include $C_1$-$C_6$-alkyl radicals or $C_1$-$C_6$-alkoxy radicals. Examples of corresponding alcohols include 3-buten-1-ol, 3-penten-1-ol, 3-methylbut-3-en-1-ol, 3-hexen-1-ol, 3-methylpent-3-en-1-ol, 3-ethylbut-3-en-1-ol and 4-methylpent-3-en-1-ol.

A preferred group of alcohols which can be isomerized advantageously by the process according to the invention is that of the 3-buten-1-ol compounds of the general formula II

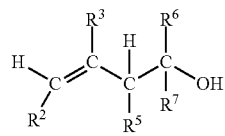

where $R^2$, $R^3$, $R^5$, $R^6$ and $R^7$ are each as defined above.

The $R^2$, $R^3$, $R^5$, $R^6$ and $R^7$ radicals are preferably alkyl radicals which have 1-6 carbon atoms and may be substituted by a hydroxyl, alkoxy or carboxyl group, more preferably hydrogen or methyl. $R^3$ and $R^6$, together with the carbon atoms between them, may also be members of an alicyclic ring, or $R^6$ may also be a cycloaliphatic, araliphatic or aromatic radical. Representatives of this group here include 3-buten-1-ol, 3-methyl-3-buten-1-ol (isoprenol), 4-formyl-3-buten-1-ol, 1,2,3-trimethyl-3-buten-1-ol, 2-isobutyl-3-buten-1-ol 3-(2'-hydroxyethyl)-3-buten-1-ol, 1-hexyl-3-buten-1-ol, 1-methylene-2-methylcyclohexan-3-ol, 1-methylene-2-ethyl-cyclopentan-3-ol, 1-methylenecyclohexan-3-ol and 1-methylenecycloheptan-3-ol.

The isomerization by the process according to the invention is preferably performed in the liquid phase. A solvent is not absolutely necessary, and it is also possible to work in the solutions of the pure starting alcohol or of mixtures of different starting alcohols.

When a separate solvent is used, useful examples have been found to be o- or p-xylene or ethers, for example diphenyl ether.

The process according to the invention is more preferably suitable for the isomerization of 3-methylbut-3-en-1-ol (isoprenol) to 3-methylbut-2-en-1-ol (prenol). In this case, it is possible with preference to isomerize in pure isoprenol or in a mixture of isoprenol and another alcohol (including prenol) or in a mixture of isoprenol and an aldehyde (e.g. 3-methylbut-2-en-1-al or prenal).

The process can be performed either in batchwise mode or in continuous mode. Preference is given to performing the process at pressures of less than 10 MPa ($10^7$ Pa), preferably less than 1 MPa ($10^6$ Pa). Preferred reaction temperatures are 0 to 150° C., preferably 10 to 100° C., and, especially in the case of isomerization of isoprenol by the process according to the invention, 20 to 80° C.

The main by-product formed in the isomerization of isoprenol by the process according to the invention is 3-methylbut-2-en-1-al (MBA or prenal), which is formed by oxidation of prenol under the oxidative conditions. Prenal can be removed and is a precursor for citral, a commercially important product.

According to the invention, the reaction is performed in an oxygenous atmosphere. As a corresponding agent, it is possible with preference to use pure oxygen or gases comprising free oxygen, especially those gases or gas mixtures with an oxygen content in the range of 2-50% by volume, preferably of 3-40% by volume and more preferably of 7-18% by volume. It is also possible to use air as a readily available oxidation medium. Alternatively, hydrogen peroxide is also suitable as an oxidizing agent.

Surprisingly, good conversions and selectivities are achieved only under oxidative conditions with the noble metal catalysts having a support material based on carbon which are used in the process according to the invention, which was surprising and unexpected in accordance with the unambiguous teaching of the prior art. Without oxygen or under inert conditions as required by the prior art, no isomerization is observed to a degree of economic interest with these supported catalysts.

According to the invention, the supported catalyst used, i.e. the catalyst applied to a support, is a catalyst which may comprise a noble metal selected from Cu, Ag, Pd, Pt, Rh, Ru, W or Os. The use of palladium or gold or mixtures of palladium and gold or mixtures of palladium or gold with other noble metals has been found to be advantageous in some cases. Especially in the case of the preferred preparation of 3-methylbut-2-en-1-ol, it is possible to achieve reaction temperatures of below 80° C., which is advantageous for the product quality and suppresses undesired side reactions.

The molar ratio of palladium and/or gold to the other noble metals is not subject to any particular restriction and can be selected freely.

In the isomerization of 3-methylbut-3-en-1-ol (isoprenol), the use of supported catalysts which comprise, as well as palladium or gold, a noble metal selected from Pt or Ru has been found to be useful.

The noble metal content of the supported catalysts which are used in the process according to the invention is not subject to any particular restriction per se, and may be in the range from 0.1 to 10% by weight, preferably in the range from 0.4 to 5% by weight and more preferably in the range from 0.6 to 3% by weight.

Suitable support materials for the catalyst are the support materials based on carbon which are described in the literature, are known per se to the person skilled in the art and have already been described above.

The supported catalysts used in accordance with the invention can be prepared by processes which are known per se to those skilled in the art and are described in the literature. For example, EP-A 172 565 or EP-A 357 292 describes a process for preparing supported silver catalysts, which can also be adjusted correspondingly for the preparation of the catalysts of the present invention. Mention should also be made here of the preparation of the supported catalysts used in the process according to the invention via what is known as the flame spraying process (description of the technology, for example, in Army Engineering Manual EM 1110-2-3401), or else a preparation based on the process described in *Angew. Chem. Int. Ed.* 2007, 47, 138-141.

Owing to the simpler mode of preparation, catalysts according to the process described in the last reference are preferred.

In a further embodiment, the present invention relates to the use of supported noble metal catalysts with a support based on carbon for isomerization of olefinically unsaturated alcohols, preferably β,γ-unsaturated alcohols to α,β-unsaturated alcohols, more preferably of isoprenol to prenal, in an oxygenous atmosphere.

For details regarding the suitable catalysts and the isomerizable alcohols, reference is made to the corresponding remarks above in connection with the process according to the invention.

Surprisingly, it is possible by the process according to the invention to isomerize olefinically unsaturated alcohols, especially β,γ-unsaturated alcohols, under oxidizing conditions with good yield and selectivity. For isomerizations of this kind, the prior art to date has always considered the exclusion of oxygen to be essential, i.e. it was necessary to work under inert or reducing conditions, which is more complex in terms of process technology and hence economically disadvantageous.

The examples which follow constitute preferred embodiments of the present invention and serve for further illustration thereof.

EXAMPLE 1

A glass autoclave was charged with isoprenol (103.8 g, 1.21 mol) and the catalyst (2.40 g, 5.0% by weight of Pd/carbon), 500 kPa (5 bar) of air were injected and the gas phase was exchanged continuously (30 l/h) at 80° C. The mixture was stirred vigorously for 0.5 h. Removal of the catalyst and analysis of the residue showed the following composition: 4.32% by weight of prenal, 38.3% by weight of isoprenol, 50.9% by weight of prenol, corresponding to 61.7% conversion, 83.4% selectivity (prenol), 7.1% selectivity (prenal) and 90.5% selectivity for products of value.

EXAMPLE 2

A glass autoclave was charged with isoprenol (103.8 g, 1.21 mol) and the catalyst (2.40 g, 5.0% by weight of Pd/carbon), 500 kPa (5 bar) of air were injected and the gas phase was exchanged continuously (30 l/h) at 60° C. The mixture was stirred vigorously for 4.4 h. Removal of the catalyst and analysis of the residue showed the following composition: 8.39% by weight of prenal, 27.1% by weight of isoprenol, 56.2% by weight of prenol, corresponding to 72.9% conversion, 78.0% selectivity (prenol), 11.6% selectivity (prenal) and 89.6% selectivity for products of value.

EXAMPLE 3

In a glass autoclave, isoprenol (103.8 g, 1.21 mol) was dissolved in diphenyl ether (60 ml), so as to give a concentration of 40% by weight of isoprenol. The catalyst (2.40 g, 5.0% by weight of Pd/carbon) was added, 500 kPa (5 bar) of air were injected and the gas phase was exchanged continuously (30 l/h) at 80° C. The mixture was stirred vigorously for 4.5 h. Removal of the catalyst and analysis of the residue gave the following composition: 10.4% by weight of prenal, 8.5% by weight of isoprenol, 17.5% by weight of prenol, corresponding to 78.7% conversion, 56.4% selectivity (prenol), 33.6% selectivity (prenal) and 90.0% selectivity for products of value.

EXAMPLE 4

A glass autoclave was charged with isoprenol (103.8 g, 1.21 mol) and the catalyst (2.40 g, 5.0% by weight of Pd/carbon), 100 kPa (1 bar) of air were injected and the gas phase was exchanged continuously (30 l/h) at 80° C. The mixture was stirred vigorously for 4.45 h. Removal of the catalyst and analysis of the residue showed the following composition: 8.22% by weight of prenal, 28.1% by weight of isoprenol, 56.9% by weight of prenol, corresponding to 71.9% conversion, 80.0% selectivity (prenol), 11.6% selectivity (prenal) and 91.6% selectivity for products of value.

EXAMPLE 5

A glass autoclave was charged with isoprenol (103.8 g, 1.21 mol) and the catalyst (2.40 g, 3.4% by weight of Pd/carbon), oxygen was injected (200 KPa (2 bar)), and the mixture was stirred vigorously at 80° C. for 4.5 h. The removal of the catalyst and analysis of the residue gave the following composition: 5.67% by weight of prenal, 35.7% by weight of isoprenol, 53.8% by weight of prenol, corresponding to 64.3% conversion, 84.5% selectivity (prenol), 8.9% selectivity (prenal) and 93.4% selectivity for products of value.

EXAMPLE 6

Comparative Example

A glass autoclave was charged with isoprenol (103.8 g, 1.21 mol) and the catalyst (2.40 g, 3.4% by weight of Pd/carbon), 500 kPa (5 bar) of nitrogen were injected and the gas phase was exchanged continuously (30 l/h) at 80° C. The mixture was stirred vigorously for 5 h. Removal of the catalyst and analysis of the residue gave the following composition: 0.56% by weight of prenal, 96.14% by weight of isoprenol, 0.47% by weight of prenol, corresponding to 3.9% conversion, 12.2% selectivity (prenol), 14.6% selectivity (prenal) and 26.8% selectivity for products of value.

EXAMPLE 7

Comparative Example

In a glass autoclave, isoprenol (2.40 g, 27.9 mmol) was dissolved in p-xylene (120 ml), so as to give a concentration of 2.3% by weight of isoprenol. Then the catalyst (2.40 g, Pd,Se/SiO$_2$) was added, 500 kPa of air (5 bar) were injected, and the mixture was stirred vigorously at 110° C. for 1.1 h. Removal of the catalyst and analysis of the residue gave the following composition: 0.01% by weight of prenal, 2.40% by weight of isoprenol, 0.01% by weight of prenol, corresponding to 11.9% conversion, 4.8% selectivity (prenol), 4.8% selectivity (prenal) and 9.6% selectivity for products of value.

The invention claimed is:
1. A process for isomerizing olefinically unsaturated alcohols over supported noble metal catalysts, which comprises performing the isomerization with a supported noble metal catalyst in an oxygenous atmosphere.

2. The process according to claim 1, wherein the support material used for the supported catalyst is a material based on carbon.

3. The process according to claim 1, wherein the noble metal is Au, Cu, Ag, Pd, Pt, Rh, Ru, W, Os or a mixture of these metals.

4. The process according to claim 3, wherein the noble metal is Pd or Au, or a mixture of Pd or Au and Cu, Ag, Pd, Pt, Ru, Rh, W or Os.

5. The process according to claim 1, wherein the oxygenous atmosphere used is oxygen, air or an oxygen-comprising gas mixture.

6. The process according to claim 1, wherein β,γ-unsaturated alcohols of the formula I are isomerized to the corresponding α,β-unsaturated alcohols

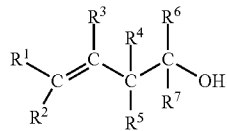

I where the substituents may each independently be hydrogen, a $C_1$-$C_8$-alkyl group, an optionally substituted $C_6$-$C_8$-cycloalkyl group or an optionally substituted $C_6$-$C_{18}$-aryl group.

7. The process according to claim 1, wherein 3-buten-1-ol compounds of the formula II

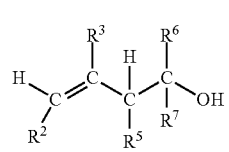

II are isomerized.

8. The process according to claim 1, wherein 3-methylbut-3-en-1-ol (isoprenol) is isomerized to 3-methylbut-2-en-1-ol (prenol).

9. A process for isomerization of olefinically unsaturated alcohols in an oxygenous atmosphere which comprises utilizing a supported noble metal catalyst with a support based on carbon.

10. The process according to claim 9, wherein 3-methylbut-3-en-1-ol is isomerized to 3-methylbut-2-en-1-ol.

* * * * *